United States Patent [19]

Kempe

[11] Patent Number: 4,658,014

[45] Date of Patent: Apr. 14, 1987

[54] SYNTHETIC PEPTIDES WITH CALCITONIN-LIKE ACTIVITY

[76] Inventor: Tomas G. Kempe, 16604 Windermere Pl., Minnetonka, Minn. 55345

[21] Appl. No.: 811,179

[22] Filed: Dec. 20, 1985

[51] Int. Cl.$^4$ ............................................... C07K 7/36
[52] U.S. Cl. ..................................... 530/307; 514/808
[58] Field of Search ......................... 530/307; 514/808

[56] References Cited

U.S. PATENT DOCUMENTS

| | | | |
|---|---|---|---|
| 3,929,758 | 12/1975 | Hughes et al. ........................ | 530/307 |
| 3,934,008 | 1/1976 | Ritter et al. ............................ | 514/11 |
| 4,086,221 | 4/1978 | Sakakibara et al. ................. | 530/307 |
| 4,514,331 | 4/1985 | Kaiser et al. ......................... | 530/317 |

Primary Examiner—Delbert R. Phillips

[57] ABSTRACT

New peptides are disclosed which have biological activity of the same type as calcitonins and which have been modified with desaminocysteine and and α-aminosuberic acid at the N-terminal and new amino acid substituents at the penultimate position of the C-terminal.

3 Claims, No Drawings

SYNTHETIC PEPTIDES WITH CALCITONIN-LIKE ACTIVITY

FIELD OF THE INVENTION

This invention relates to peptides having calcitonin-like activity and to peptides which can be converted to biologically active peptides with calcitonin-like activity.

BACKGROUND OF THE INVENTION

There is a wide variation in activity in naturally occuring calcitonins with an approximate 40-fold range in biopotency. All natural calcitonins share some structural features. Each is 32 amino acids long with a C-terminal prolinamide and an N-terminal disulfide linked ring from position 1 through 7. Salmon 1 calcitonin, for example, has the following formula (Niall, H. D.(1969)Proc. Natl. Acad. Sci. USA 64,771-778):

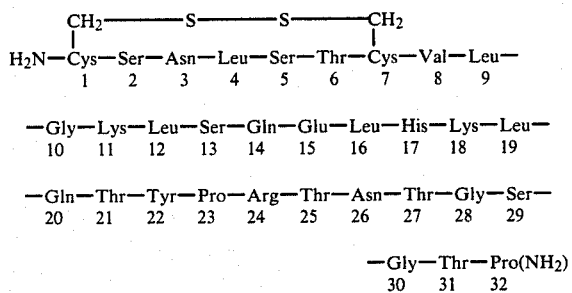

Other calcitonins occuring in nature resemble salmon 1 calcitonin in varying degrees (Queener, S. F. and Bell, N. H. (1975)Metabolism 24,555-567; Lasmoles, F. et al.(1985)Febs Lett. 180,113-116). Eel calcitonin differs from salmon 1 calcitonin by having the amino acid Asp at position 26, Val at position 27 and Ala at position 29. Chicken calcitonin differs from salmon 1 calcitonin by having the amino acid Ala at position 2, Ser at position 3, Asp at position 26, Val at position 27 and Ala at position 29. Salmon 2 calcitonin differs from salmon 1 calcitonin by having Asp at position 15, Phe at position 22, Ala at position 29 and Val at position 31. Salmon 3 calcitonin differs from salmon 1 calcitonin by having Met at position 8, Asp at position 15, Phe at position 22, Ala at position 29 and Val at position 31. The calcitonins of mammalian origin differ more markedly from salmon 1 calcitonin, as shown in the references above. The structural features responsible for the increased potency ( about 40 times) of ultimobranchial calcitonins relative to calcitonins of mammalian origin have not yet been fully determined.

Modifications of the N-terminal cysteine by acylation or by substitution with 3-mercaptopropionic acid (desaminocysteine) show slight increases in the hypocalcemic activity of human calcitonin (Rittel, W. et al. (1976) Experientia 32,246-248; U.S. Pat. No. 3,934,008). The replacement of both cysteines with L-α-aminosuberic acid (Asu) at position 7 in the calcitonin sequence generated an analog with an ethylene bond instead of the naturally occuring disulfide bond between residue 1 and 7. The Asu analog also lack the α-amino group and is thus isosteric to the 3-mercapto analog above. The [Asu$^{1,7}$] eel calcitonin analog has comparable activity to the naturally occuring hormone with the disulfide bond. The [Asu$^{1,7}$] analog offers many advantages in large scale peptide synthesis due to the stability of a carbon-carbon bond compared with the reactive sulfur-sulfur bond (Morikawa, T. et al. (1976)Experientia 32, 1104-1106; Yamauchi, H. et al. (1977) Endocrinol. Japan 24,281-285; Yamamoto, I. et al. (1981) Endocrinol. 108,698-702; Ohno, H. et al. (1981) Japan J. Pharmacol. 31,537-542; U.S. Pat. No. 4,086,221).

SUMMARY OF THE INVENTION

It has been discovered that compounds of the Formula I:

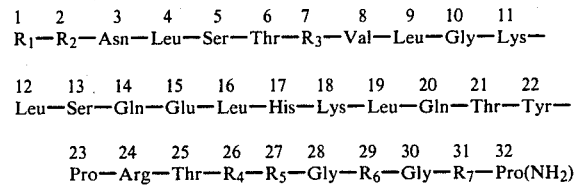

wherein, $R_1$ is 3-mercaptopropionic acid and $R_3$ is Cys and $R_1$-$R_3$ is linked by a —S—S— bond or, $R_1$ is hydrogen ($R_2$ the first α-amino acid) and $R_3$ is Asu and $R_2$-$R_3$ is linked by a —CH$_2$—CH$_2$— bond, $R_2$ is an optional moiety from the group consisting of Ser, Ala, and Gly when present, $R_4$ is Asn or Asp, $R_5$ is Thr or Val, $R_6$ is Ser or Ala, $R_7$ is Ser, Asn, Asp, Glu, Gln, Pro or Hse, have biological activity of the same type as known calcitonins (e.g. lowering plasma calcium levels). The new peptides have good potency and quality when compared with known calcitonins and to peptides reported to have calcitonin like activity.

A preferred peptide is the Asu$^{1,7}$ analog of the Formula II:

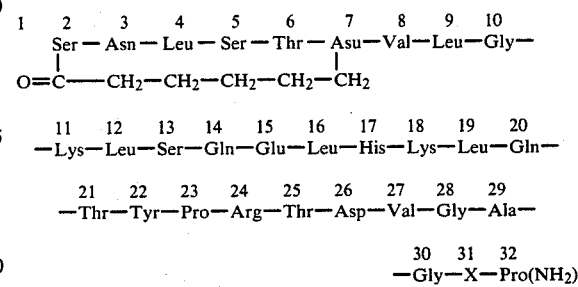

in which X is, Ser, Asp, Asn, Glu, Gln, Pro and Hse. Particularly preferred peptides of the invention are the analogs wherein X is, Ser, Asp and Hse. The basic amino acid residues, Lys, Arg and His of the compound of Formula I may be in the form of their non-toxic acid addition salts such as ammonium acetates and ammonium chlorides.

DESCRIPTION OF THE INVENTION

The compound of Formula I may be synthesized by methods well-known to those skilled in the art of peptide synthesis, e.g. solution phase synthesis (see Finn, F. M. and Hofmann, K., in *Proteins*, Vol. 2, 3rd Ed., H. Neurath and R. L. Hill, eds. (Academic Press, New York, 1976), pp 105-253), or solid phase synthesis (see Barany, G. and Merrifield, R. B. in *The Peptides*, Vol. 2, E. Gross and J. Meienhofer, eds. (Academic Press, New York, 1979) pp 3–284). Preferably the synthesis may follow the stepwise solid phase strategy reported by Merrifield, R. B. (1963) J. Am. Chem. Soc. 85,2149–2154, the teachings of which are incorporated herein by reference.

The acid labile tert-butyloxycarbonyl (Boc—) group may be used for temporary α-N protection and the more acid stable groups may be used for protection of the side chains of the amino acids. Amino acid derivatives are listed in Table 1 and abbreviations are listed in Table 2. Attachment of the peptide chain to a copolymer matrix of styrene and 1% divinylbenzene may employ a benzhydrylamine type handle as reported in Pietta, P. G. et al. (1970) Chem. Commun. 650–651; Hruby, V. J. et al. (1977) J. Org. Chem. 42,3552–3556; and Tam, J. P. et al. (1981) Tetrahedron Lett. 22,2851–2854, which teachings also are incorporated by reference. All amino acids may be incorporated following a double coupling protocol with some modifications for particular amino acids. For all reactions, except for arginine, asparagine and glutamine, the first coupling employs the preformed symmetric anhydride method (Hagenmaier, H and Frank, H (1972) Hoppe-Seyler's Z. Physiol. Chem. 353,1973–1976) in dichloromethane and the second coupling employs the preformed hydroxybenztriazole ester method (Konig, W. and Geiger, R. (1970) Chem. Ber. 103,788–798) in dimethyl formamide (DMF). For Boc-Arg(Tos), standard DCC coupling conditions are employed to reduce the risk of lactam formation. The second coupling is done with active HOBt ester method in DMF. Boc-Asn and Boc-Gln were exclusively coupled as HOBt esters in DMF to reduce nitrile and amidine formation (Mojsov, S. et al (1980) J. Org. Chem. 45,555–560). $N^\epsilon$-(2-Chlorobenzyloxycarbonyl)lysine, Lys(ClZ), is used because it is more stable than the benzyloxycarbonyl derivative to the acid deprotection steps and it also avoids side chain branching (Erickson, B. W. and Merrifield, R. B. (1972) J. Am. Chem. Soc. 95,3757–3763). The β-cyclohexylester (cHex) of Boc-Asp-OH is used; it is also more stable to acids and thus minimizes aspartimide formation (Tam, J. P. (1979) Tetrahedron Lett. 4033–4036). The quantitative ninhydrin test is routinely used throughout the synthesis to monitor the extent of coupling after each cycle (Sarin, V. K. et al. (1981)Anal. Biochem. 117,147–157). If $R_3$ is to be L-α-aminosuberic acid (Asu) the amino group and the C-8 carboxyl group are first protected. The Asu derivative is coupled to residue 8 using coupling procedure A which is described in detail in Example 1. After completion of the synthesis by residue 2 (see Table 1) the C-8 carboxylic group on Asu is then deprotected to allow it to react with the N-terminal amino group of residue 2.

TABLE 1

Amino acid derivatives for the synthesis of a peptide of the Formula 1, with calcitonin-like activity (Example 1).

| cycle nr. and amino acid | protected amino acid | MW | mMol | g | coupling procedure |
|---|---|---|---|---|---|
| 32 | Pro—benz-hydryl amine resin | | 1 | 2 | |
| 31,13,5,2 | Boc—Ser(Bzl) | 295.1 | 8 | 2.36 | A |
| | | | 4 | 1.18 | |
| 30,28 10 | Boc—Gly | 175.2 | 8 | 1.4 | A |
| | | | 4 | 0.7 | |
| 25,21,6 | Boc—Thr(Bzl) | 309.1 | 8 | 2.48 | A |
| | | | 4 | 1.24 | |
| 3 | Boc—Asn | 232.2 | 4 | 0.93 | B |

TABLE 1-continued

Amino acid derivatives for the synthesis of a peptide of the Formula 1, with calcitonin-like activity (Example 1).

| cycle nr. and amino acid | protected amino acid | MW | mMol | g | coupling procedure |
|---|---|---|---|---|---|
| 24 | Boc—Arg(Tos) | 442.5 | 4 | 1.77 | C |
| 23 | Boc—Pro | 215.1 | 8 | 1.72 | A |
| | | | 4 | 0.86 | |
| 22 | Boc—Tyr (Cl$_2$Bzl) | 441.2 | 8 | 3.53 | A |
| | | | 4 | 1.76 | |
| 20,14 | Boc—Gln | 246.3 | 4 | 0.98 | B |
| 19,16,12,9,4 | Boc—Leu | 249.2 | 8 | 2.0 | A |
| | | | 4 | 1.0 | |
| 18,11 | Boc—Lys (Cl—Z) | 314.8 | 8 | 2.5 | A |
| | | | 4 | 1.26 | |
| 17 | Boc—His(Tos) | 409.2 | 8 | 3.28 | A |
| | | | 4 | 1.64 | |
| 15 | Boc—Glu (OcHex) | 342.4 | 8 | 2.74 | A |
| | | | 4 | 1.37 | |
| 27,8 | Boc—Val | 217.1 | 8 | 1.74 | A |
| | | | 4 | 0.87 | |
| 7 | Boc—Cys (4-Me—Bzl) | 325.2 | 8 | 2.6 | A |
| | | | 4 | 1.3 | |
| 29 | Boc—Ala | 189.2 | 8 | 1.51 | A |
| | | | 4 | 0.76 | |
| 26 | Boc—Asp (OcHex) | 328.4 | 8 | 2.63 | A |
| | | | 4 | 1:31 | |
| 1 | 3-(4-Me—Bzl) thio propionic acid | 211.2 | 8 | 1.70 | A |
| | | | 4 | 0.85 | |

TABLE 2

Abbreviations (Biochem. Biophys. Acta 133, 1–5 (1967))

| | |
|---|---|
| Boc = | tert-butyloxycarbonyl |
| Bzl = | benzyl |
| Tos = | tosyl |
| Cl$_2$Bzl = | 2,6-dichlorobenzyl |
| Cl—Z = | o-chlorobenzyloxycarbonyl |
| OcHex = | B-cyclohexyl ester |
| 4-Me—Bzl = | 4-methylbenzyl |
| HOBt = | N—hydroxybenztriazole |
| DIEA = | diisopropylethylamine |
| DCC = | dicyclohexylcarbodiimide |
| DMF = | N,N—dimethylformamide |
| CM = | carboxymethyl |
| TFA = | trifluoroacetic acid |
| HPLC = | high performance liquid chromatography |
| MRC units = | Medical Research Council units standard |
| Pro = | L-prolyl |
| Ser = | L-seryl |
| Gly = | glycyl |
| Thr = | L-threonyl |
| Asn = | L-asparaginyl |
| Arg = | L-arginyl |
| Tyr = | L-thyronyl |
| Gln = | L-glutaminyl |
| Leu = | L-leucyl |
| Lys = | L-lysyl |
| His = | L-histidyl |
| Glu = | L-glutamyl |
| Val = | L-valyl |
| Cys = | L-cysteinyl |
| Ala = | L-alanyl |
| Asp = | L-aspartyl |
| Hse = | L-homoseryl |
| Asu = | L-u-aminosuberyl |

For details on methods of incorporating Asu in the proper positions, see Morikawa, T. et al. (1976) Experientia 32,1104–1106. Boc-Hse(Bzl) may be synthesized following published procedure (Turan, A. and Manning, M. (1977) J. Med. Chem. 20,1169–1172). The thiol group of 3-mercaptopropionic acid may be protected by benzyl groups (Brese, C. and Dupuis, G. (1965) Can. J. Chem. 43,2174–2179), preferably derivatives for the thiol group in cysteine are used (Table 1).

RESIN PEPTIDE CLEAVAGE AND PURIFICATION

Cleavage of the peptides from the resin and removal of all the remaining protecting groups is accomplished by treatment with anhydrous hydrogen fluoride in the presence of anisole (Yamashiro, D and Li, C. H. (1978) J. Am. Chem. Soc. 100,5174–5179). Crude peptide is removed from the resin by washing with 10% aqueous acetic acid and is then lyophilized. When the intramolecular disulfide bond in the peptide is present, the residue may be treated with dithiothreitol and the disulfide between residues 1 and 7 can be formed by diluting the solution several-fold and adding potassiumferricyanide in aqueous solution. The resultant peptide solution is then concentrated by passing it through a CM-Sephadex, C-25 column and then eluting with a linear gradient of sodium chloride from zero to 0.3 Molar in phosphate buffer (Live, D. H. et al. (1977)J. Org. Chem. 42,3556–3561; Moe, G. R. and Kaiser, E. T.(1985)Biochemistry 24,1971–1976). The sample is finally desalted by gel filtration, concentrated and isolated by HPLC.

While the peptide at the N-terminal may be the [$Asu^{1,7}$] analog, for exemplification, the following detailed disclosure is directed to the isosteric 3-mercaptopropionic acid analog (desaminocysteine). The formula for this new peptide having activity of the same type as calcitonins may be written as follows:

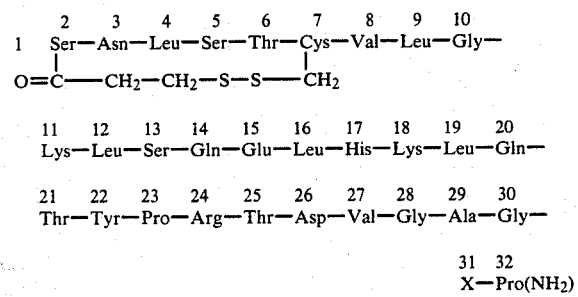

in which X is Ser, Asp, Asn, Glu, Gln, Pro and Hse.

As may be seen from the formula above, 32 amino acids are involved and in this formula, the positions are numbered according to the accepted procedure beginning at position 1 for mercaptopropionic acid on one end of the chain and ending with prolinamide at position 32 at the other end of the chain. For clarity of description, this same numbering system will be followed in referring to the cycles of the synthesis. The assembly of the amino acids begins with cycle 31 which involves the coupling of the amino acid to the proline moiety, followed by residue 30 and so on to the last amino acid. Protected amino acid derivatives that may be used in the synthesis of the peptide of Formula I are given in Table I. The resin which was functionalized with proline is available from chemical supply houses.

As indicated earlier, three types of coupling procedures are used, depending on the properties of the reactants. In Table I, the amino acid position and cycle number, type of coupling procedure, molecular weights and amount of reactants for the cycle are given. The details for each coupling protocol A, B, and C are described below.

RESIN PEPTIDE SYNTHESIS

Example 1

A peptide of Formula I, wherein $R_1$ is 3-mercaptopropionic acid and $R_3$ is Cys and $R_1$–$R_3$ is linked by a disulfide bond (—S—S—), $R_2$ is Ser, $R_4$ is Asp, $R_5$ is Val, $R_6$ is Ala and $R_7$ is Ser, see Table I.

Double coupling protocol using symmetric anhydride and active ester methods may be used to ensure as complete coupling as possible. The following protocol may be used for all amino acids except for arginine, asparagine and glutamine. The protocol is given for 2 g benzhydryl type resin functionalized with a total of 1 mMol of proline.

Coupling Procedure A

1. The resin is washed with dichloromethane, $CH_2Cl_2$, (30 mL, 6×1 min).
2. Removal of the Boc protecting group is done with 50% TFA in $CH_2Cl_2$ (30 mL, 3×1 min) and with 30 mL for 20 min.
3. The reagent is then removed with $CH_2Cl_2$ wash (30 mL, 6×1 min).
4. Traces of acid are finally removed with 5% DIEA in $CH_2Cl_2$ (30 mL, 2×2 min).
5. A final wash is done before the coupling is completed, $CH_2Cl_2$ (30 mL, 6×1 min).
6. 5 mg of the resin are removed for ninhydrin test.
7. The protected amino acid (listed in Table I, 8 mMol) dissolved in 10 mL of $CH_2C_2$ is then treated with DCC (4 mMol, 825 mg) in 3 mL of $CH_2Cl_2$. After 10 min, the solution is filtered and added to the resin. The precipitate is washed with 10 mL of $CH_2Cl_2$ and added to the reaction vessel which is then shaken for 2 h at room temperature.
8. The resin is washed with $CH_2Cl_2$ (30 mL, 4×2 min).
9. The resin is washed with 5% DIEA in $CH_2Cl_2$ (30 mL, 2 min).
10. The resin is washed with $CH_2Cl_2$ (30 mL, 4×2 min).
11. Ninhydrin test is performed.
12. The resin is washed with DMF (30 mL, 2×2 min).
13. HOBt (4 mMol, 540 mg) in 7 mL of DMF at 0° C. is mixed with DCC (4 mMol, 825 mg) in 3 mL $CH_2Cl_2$. The protected amino acid (listed in Table I, 4 mMol) dissolved in 6 mL of DMF is then added. The mixture is kept at 10 min at 0° C. and is then added to the resin. The mixture is shaken for 2 h at room temperature.
14. The resin is then washed with DMF (30 mL, 2×2 min).
15. The resin is washed with $CH_2Cl_2$ (30 mL, 4×1 min).
16. The resin is washed with 5% DIEA in $CH_2Cl_2$ (30 mL, 2 min).
17. The resin is washed with $CH_2Cl_2$ (30 mL, 3×1 min).
18. Ninhydrin test is performed.

Coupling Procedure B (Used for the amino acids asparagine and glutamine):
Steps 1–6 were the same as coupling procedure A.
7. The resin is washed with DMF in $CH_2Cl_2$ (1:2 v/v, 30 mL, 2×2 min).
8. To HOBt (4 mMol, 540 mg) in 7 mL DMF/$CH_2Cl_2$ (1:1 v/v) at 0° C. is added DCC (4 mMol, 825 mg) in 3 mL of $CH_2Cl_2$. To that mixture is then added the protected amino acid (listed in Table 1, 4 mMol) in 6 mL of DMF/$CH_2Cl_2$. The reaction mixture is added to the resin after 10 min at 0° C. The resin is then shaken for 2 h at room temperature.

9. The resin is washed with DMF/CH$_2$Cl$_2$ (1:2 v/v, 30 mL, 2×2 min).

The steps 8–18 described in coupling procedure A are then followed.

Coupling Procedure C (Used for the amino acid arginine)

Steps 1–6 are the same as coupling procedure A.

7. The protected amino acid (listed in Table 1, 4 mMol) in 10 mL CH$_2$Cl$_2$ is added to the resin. DCC (4 mMol, 825 mg) in 3 mL CH$_2$Cl$_2$ is added after 5 min to the resin. The reaction mixture is then shaken for 2 h at room temperature.

The steps 8–18 described in coupling procedure A are then followed.

The addition of 3-mercaptopropionic acid represents the completion of the solid phase synthesis. The Boc group is finally removed by steps 1–6 in coupling procedure A. The resin peptides are then removed from the reaction vessel and dried in vacuum. Cleavage and purification steps are carried out as follows:

RESIN-PEPTIDE CLEAVAGE

The dried resin peptide (2 g) and 2 mL of anisole are placed in a teflon reaction vessel which is cooled in dry ice-acetone bath and about 15 mL of hydrogen fluoride gas is condensed into the vessel. The mixture is stirred at 0° C. in an ice bath for 45 min. The hydrogen fluoride is then evaporated under vacuum, using first a water aspirator and later a high vacuum pump. The residue is triturated with 5×30 mL of ethyl acetate, and the peptide was extracted from the resin beads with 100 mL of 10% aqueous acetic acid solution. The mixture was lyophilized to dryness.

PURIFICATION OF CRUDE PEPTIDES

A 100 mg sample of the lyophilized peptide is treated with excess dithiothreitol (5 mMol) in 5 mL of 50 mM sodium phosphate buffer at pH 7.5 for 1 h at room temperature. The intramolecular disulfide bond between residues 1 and 7 is formed by diluting the peptide solution to volume of 1 liter in the same buffer. A solution of 20 mM K$_3$Fe(CN)$_6$ is added with stirring until a persistant yellow color is obtained. The resultant dilute peptide solution is concentrated by passing it through a CM-Sephadex, C-25 column and then eluting with a linear gradient of NaCl from zero to 0.3M employing the same buffer. Fractions from this column may be desalted on a Sephadex G-15 column, eluting with a 0.03M aqueous acetic acid solution. Samples for biological testing are isolated on an analytical HPLC (column: Altex ODS, 5 micron, 4.6×250 mm, flow 1.5 mL/min, gradient of 30–45% acetonitrile in 0.1M ammonium acetate at pH 5.5). The isolated peptide samples may be quantified using salmon 1 calcitonin as a reference sample.

The HPLC isolated samples are hydrolyzed with 5.5M hydrochloric acid, and amino acid analysis are performed to confirm the chemical composition.

The new peptides are biologically active and are useful in lowering the content of calcium in plasma, as indicated by standard tests in rats (Kumar, M. A. et al. (1965) J. Endocrinol. 33,469–475). While only certain embodiments of my invention have been described in specific details, it will be apparent to those skilled in the art that many other specific embodiments may be practiced and many changes may be made, all within the spirit of the invention and the scope of the appended claims.

What is claimed is:

1. A biologically active peptide with calcitonin-like activity having the formula:

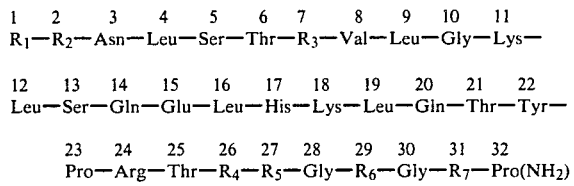

wherein,

R$_1$ is 3-mercaptopropionic acid and R$_3$ is Cys and R$_1$–R$_3$ is linked by a —S—S— bond, or R$_1$ is hydrogen and R$_3$ is Asu and R$_2$–R$_3$ is linked by a —CH$_2$—CH$_2$— bond, R$_2$ is an optional moiety from the group consisting of Ser, Ala and Gly, R$_4$ is Asn or Asp, R$_5$ is Thr or Val, R$_6$ is Ser or Ala, R$_7$ is Ser, Asn, Asp, Glu, Gln, Pro or Hse.

2. A biologically active peptide with calcitonin-like activity having the formula:

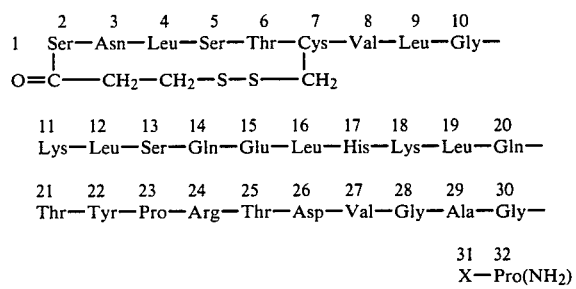

wherein X is Ser, Asp, Asn, Glu, Gln, Pro or Hse.

3. A biologically active peptide with calcitonin-like activity having the formula:

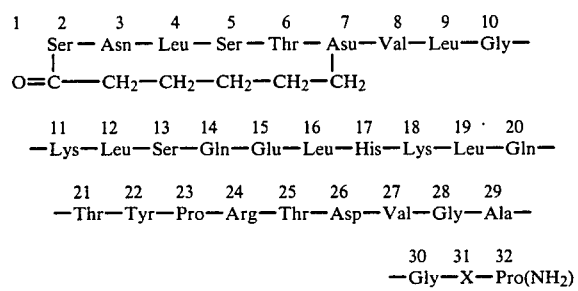

wherein X is Ser, Asp, Asn, Glu, Gln, Pro or Hse.

* * * * *